US009125982B2

(12) United States Patent
Frey

(10) Patent No.: US 9,125,982 B2
(45) Date of Patent: Sep. 8, 2015

(54) METHODS AND SYSTEMS FOR PROVIDING METERED DOSES OF A COMPOUND TO AN INDIVIDUAL

(75) Inventor: Daniel John Frey, Needham, MA (US)

(73) Assignee: FLOWONIX MEDICAL INCORPORATED, Mount Olive, NJ (US)

( * ) Notice: Subject to any disclaimer, the term of this patent is extended or adjusted under 35 U.S.C. 154(b) by 991 days.

(21) Appl. No.: 12/556,184

(22) Filed: Sep. 9, 2009

(65) Prior Publication Data

US 2011/0060318 A1    Mar. 10, 2011

(51) Int. Cl.
 *A61M 5/168*    (2006.01)
 *A61M 5/142*    (2006.01)
 *A61M 5/148*    (2006.01)

(52) U.S. Cl.
 CPC ......... *A61M 5/14276* (2013.01); *A61M 5/1483* (2013.01); *A61M 5/16809* (2013.01); *A61M 2205/8212* (2013.01); *A61M 2205/8231* (2013.01)

(58) Field of Classification Search
 CPC .......... A61M 5/14276; A61M 5/1483; A61M 5/16809; A61M 2205/8212; A61M 2205/8231
 USPC ........... 604/891.1, 93.01, 181, 183, 186, 245, 604/246, 288.01, 288.03, 288.04
 See application file for complete search history.

(56) References Cited

U.S. PATENT DOCUMENTS 3,840,278 A * 10/1974 Fleischer et al. ............. 303/168
4,373,527 A    2/1983 Fischell
4,838,887 A *  6/1989 Idriss ......................... 604/891.1
5,879,375 A    3/1999 Larson, Jr. et al.
6,826,365 B1  11/2004 Constable
6,916,159 B2   7/2005 Rush et al.
7,278,983 B2  10/2007 Ireland et al.
7,452,354 B2  11/2008 Bright et al.

OTHER PUBLICATIONS

International Search Report and Written Opinion regarding PCT/US2010/040299, dated Sep. 1, 2010 (12 pages).
International Preliminary Report on Patentability issued in PCT Application No. PCT/US2010/040299, mailed on Mar. 22, 2012.

* cited by examiner

*Primary Examiner* — Nicholas Lucchesi
*Assistant Examiner* — Melissa A Snyder
(74) *Attorney, Agent, or Firm* — The Marbury Law Group, PLLC

(57) ABSTRACT

An implantable pump for providing metered doses of a compound to an individual is described. The implantable pump includes a chamber for storing an individual dose of the compound, an inlet valve fluidly coupled to the chamber for controlling a flow of the compound into the chamber, and an outlet valve fluidly coupled to the chamber for controlling a flow of the compound out of the chamber and into the individual. The pump includes an inlet valve driver circuit operable for opening and closing the inlet valve, and an outlet valve driver circuit operable for opening and closing the outlet valve. A battery and a charging circuit that includes a capacitor are included in the implantable pump. The charging circuit is operatively coupled to the battery for charging of the capacitor. The charged capacitor is operable for supplying power to the valve driver circuits.

17 Claims, 6 Drawing Sheets

METHODS AND SYSTEMS FOR PROVIDING METERED DOSES OF A COMPOUND TO AN INDIVIDUAL

BACKGROUND

The field of the invention relates generally to pumping devices, and more specifically, to methods and systems for providing metered doses of a compound to an individual.

Use of implantable pumps for treating chronic pain conditions has become widely accepted practice when more conservative means of relieving pain are insufficient. Implantable pump technology is divided into two primary categories, namely constant flow and programmable. Both technologies incorporate an indwelling catheter to establish a fluid path from a pump disposed subcutaneously to a desired anatomical site, including but not limited to, arterial or venous locations, the epidural space and the intrathecal space of the spine. The success of an implanted pump system is dependent in large part on successful and dependable pump operation.

BRIEF DESCRIPTION

In one aspect, an implantable pump for providing metered doses of a compound to an individual is provided. The implantable pump includes a chamber for storing an individual dose of the compound, and an inlet valve fluidly coupled to the chamber for controlling a flow of the compound into the chamber. The implantable pump further includes an inlet valve driver circuit operable for opening and closing the inlet valve, an outlet valve fluidly coupled to the chamber for controlling a flow of the compound out of the chamber and into the individual, and an outlet valve driver circuit operable for opening and closing the outlet valve. A battery and a charging circuit including a capacitor are provided within the implantable pump. The charging circuit is operatively coupled to the battery for charging of the capacitor. The capacitor, when charged, is operable for supplying power to the inlet valve driver circuit and the outlet valve driver circuit. In embodiments, the implantable pump may further include a programmable device programmed to cause the inlet valve driver circuit to open the inlet valve; cause the inlet valve driver circuit to close the inlet valve after a predetermined length of time has passed since the inlet valve driver circuit caused the inlet valve to open; cause the outlet valve driver circuit to open the outlet valve a predetermined length of time after causing the inlet valve driver circuit to close the inlet valve; and cause the outlet valve driver circuit to close the outlet valve after a predetermined length of time has passed since the outlet valve driver circuit caused the outlet valve to open. In embodiments, the programmable device may include a wireless interface, and the programmable device can be reprogrammable via instructions received via the wireless interface. The instructions may include instructions to be executed by the programmable device that set an amount of time the inlet valve driver circuit causes the inlet valve to be open; instructions to be executed by the programmable device that set an amount of time the outlet valve driver circuit causes the outlet valve to be open; instructions to be executed by the programmable device that set an amount of time between closure of the inlet valve and opening of the outlet valve; and instructions to be executed by the programmable device that set an amount of time between closure of the outlet valve and opening of the inlet valve.

In another aspect, a method for operating an implantable pump is provided. The implantable pump includes an inlet valve, an outlet valve, an inlet valve driver circuit, an outlet valve driver circuit, a charging circuit that includes a storage capacitor for supplying a voltage to the valve driver circuits, and a battery for operating the charging circuit. The method includes charging the capacitor in the charging circuit using the battery, operating the inlet valve driver circuit, using the charged capacitor, to open the inlet valve. The provided method also includes maintaining the inlet valve in an open configuration to allow a compound stored in a reservoir to pass into an accumulator, operating the inlet valve driver circuit to close the inlet valve, charging the capacitor in the charging circuit using the battery, operating the outlet valve driver circuit, and using the charged capacitor to open the outlet valve. The method further includes maintaining the outlet valve in an open configuration to allow a compound stored in the accumulator to pass into a user of the implantable pump, and operating the outlet valve driver circuit to close the outlet valve.

In still another aspect, a circuit for controlling operation of an inlet valve and an outlet valve of an implantable pump is provided. The inlet valve is operable to allow a metered dose of a compound to pass from a reservoir to an accumulator, and the outlet valve is operable to allow the metered dose to pass from the accumulator into a user of the implantable pump. The circuit includes an inlet valve driver circuit operable for opening and closing the inlet valve, an outlet valve driver circuit operable for opening and closing the outlet valve, a battery, and a charging circuit that includes a capacitor. The charging circuit is operatively coupled to the battery for charging of the capacitor. The capacitor is operable for supplying power to the inlet valve driver circuit and the outlet valve driver circuit and further operable for preventing the battery from directly supplying current to the inlet valve driver circuit and the outlet valve driver circuit. The circuit may include a programmable device operable to execute instructions that control an amount of time the inlet valve driver circuit causes the inlet valve to be open; execute instructions that control an amount of time the outlet valve driver circuit causes the outlet valve to be open; execute instructions that control an amount of time between operating the inlet valve driver circuit to close the inlet valve and operating the outlet valve driver circuit to open the outlet valve; and execute instructions that control an amount of time between operating the outlet valve driver circuit to close the outlet valve and operating the inlet valve driver circuit to open the inlet valve. The circuit may include a programmable device operable to control operation of the inlet valve driver circuit, the outlet valve driver circuit, and the charging circuit, where the programmable device comprises a wireless interface, and the programmable device is reprogrammable based on instructions received at the wireless interface.

The features, functions, and advantages that have been discussed can be achieved independently in various embodiments of the present invention or may be combined in yet other embodiments, further details of which can be seen with reference to the following description and drawings.

DETAILED DESCRIPTION

The embodiments described herein are directed to methods and systems for providing metered doses of a compound to an individual, specifically through utilization of an implantable pump that incorporates a circuit for charging a capacitor. As further described herein, the implantable pump is programmable for controlling the dosages supplied to a user of the pump. The charged capacitor is utilized to operate inlet and outlet valve driver circuits, which in turn control operation of valves within the pump. The valves directly control the administration of the compound(s) to the user.

Figure 1:
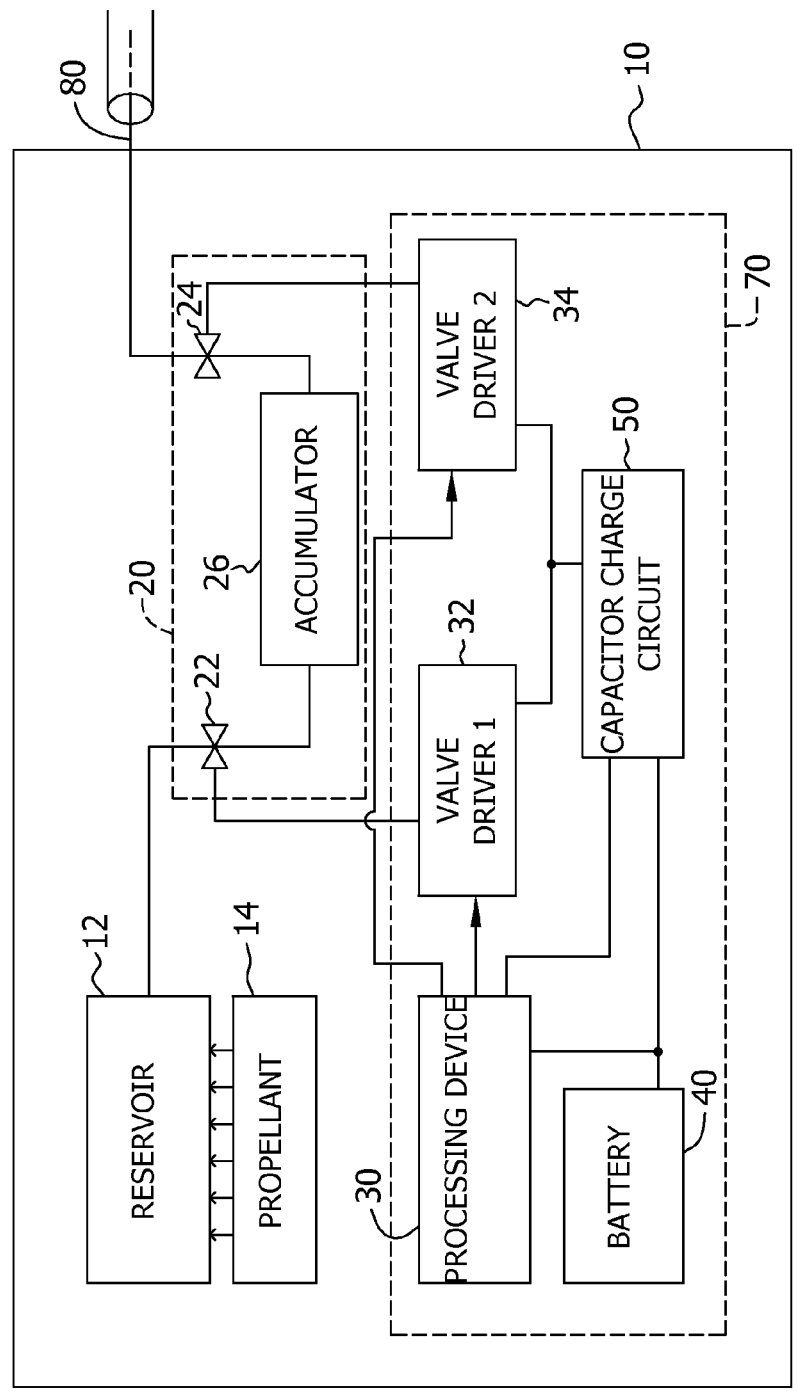
FIG. 1 is a block diagram of an implantable programmable pump.

FIG. 1 is a block diagram of an implantable programmable pump 10. Pump 10 includes a drug reservoir 12 and a propellant chamber 14. Pump 10 further includes a metering mechanism 20 that includes an inlet valve 22 fluidly coupled to reservoir 12, an outlet valve 24, and an accumulator 26 positioned between inlet valve 22 and outlet valve 24. Accumulator 26 is in fluid communication with both inlet valve 22 and outlet valve 24. In one embodiment, accumulator 26 is referred to as a compliant chamber, and has a known volume. In alternative embodiments, reservoir 12 is divided into multiple sections, as certain drugs are not to be mixed together until they are delivered to the intended target site.

At body temperature, propellant chamber 14 exerts a constant pressure on drug reservoir 12. This pressure forces the contents of reservoir 12 to flow through a filter (not shown) to inlet valve 22, which in one embodiment is a solenoid valve. As further described herein, a programmable device 30 and a first valve driver circuit 32 are utilized to open inlet valve 22 for a predetermined length of time such that accumulator 26 is filled with a portion of the contents of drug reservoir 12. Programmable device 30 subsequently controls first valve driver circuit 32 to close inlet valve 22, and after an appropriate delay, causes a second valve driver circuit 34 to open outlet valve 24, which after another programmed delay is closed. While outlet valve 24 is open, the contents of accumulator 26 are dispensed to the user of pump 10. Programmable device 30 operates via a battery 40 which also operates a capacitive charging circuit 50. Capacitive charging circuit 50 is utilized to supply power to valve driver circuits 32 and 34, from a charged capacitor, as further described herein. Operation of pump 10, as described above, provides for a metered dose of a compound, for example a medication, to be provided to a user of pump 10. The compound passes through outlet valve 24 and into, for example, a catheter in fluid communication with a particular location in the individual into which pump 10 has been implanted (such as the bloodstream).

In one embodiment, programmable device 30, valve driver circuits 32 and 34, battery 40 and capacitor charging circuit 50 are collectively referred to as an electronics module 70 which controls the operation of actuators associated with inlet valve 22 and outlet valve 24. As described above, electronics module 70 includes a programmable device 30 which may be embodied as a microprocessor executing a program or an application specific integrated circuit programmed to carry out the actions described herein.

The sequence of opening and holding inlet valve 22 open while allowing accumulator 26 to fill with the compound, closing inlet valve 22, and then opening and holding outlet valve 24 open while accumulator 26 empties, delivers a single dose of the compound, which is fixed in volume, to outlet 80 of pump 10. The rate at which the compound is delivered to a user can be varied through programming of programmable device 30 which controls the interval between actuations of both inlet valve 22 and outlet valve 24.

In one embodiment, the operating parameters of pump 10 are set using an external device that communicates with programmable device 30 within pump 10 via a wireless link. For example, and in one embodiment, valve driver circuits 32 and 34 are individually controlled using a byte in a memory mapped I/O of programmable device 30. More specifically, each valve driver utilizes three bits of this byte for controlling operation of the respective valves 22 and 24.

A seventh bit of this byte in the memory mapped I/O enables capacitor charging circuit 50. Capacitor charging circuit 50 is attached to battery 40 and operates to increase the voltage received from battery 40 for storage within a capacitor, such as capacitor 52 (shown in FIG. 2) which is shown as being within capacitor charging circuit 50. The increased voltage value to which capacitor 52 is charged is of a value that is compatible with a time-current profile associated with the individual valves and valve driver circuits. An interlock circuit (not shown) is described below that utilizes logic to prevent valves 22 and 24 (actually valve driver circuits 32 and 34) from being actuated simultaneously. The interlock circuit also prevents valve actuation during the charge time associated with capacitor charging circuit 50. The programming associated with programmable device 30 is utilized to set the times and durations associated with the above described valve opening and closing sequences.

Figure 2:
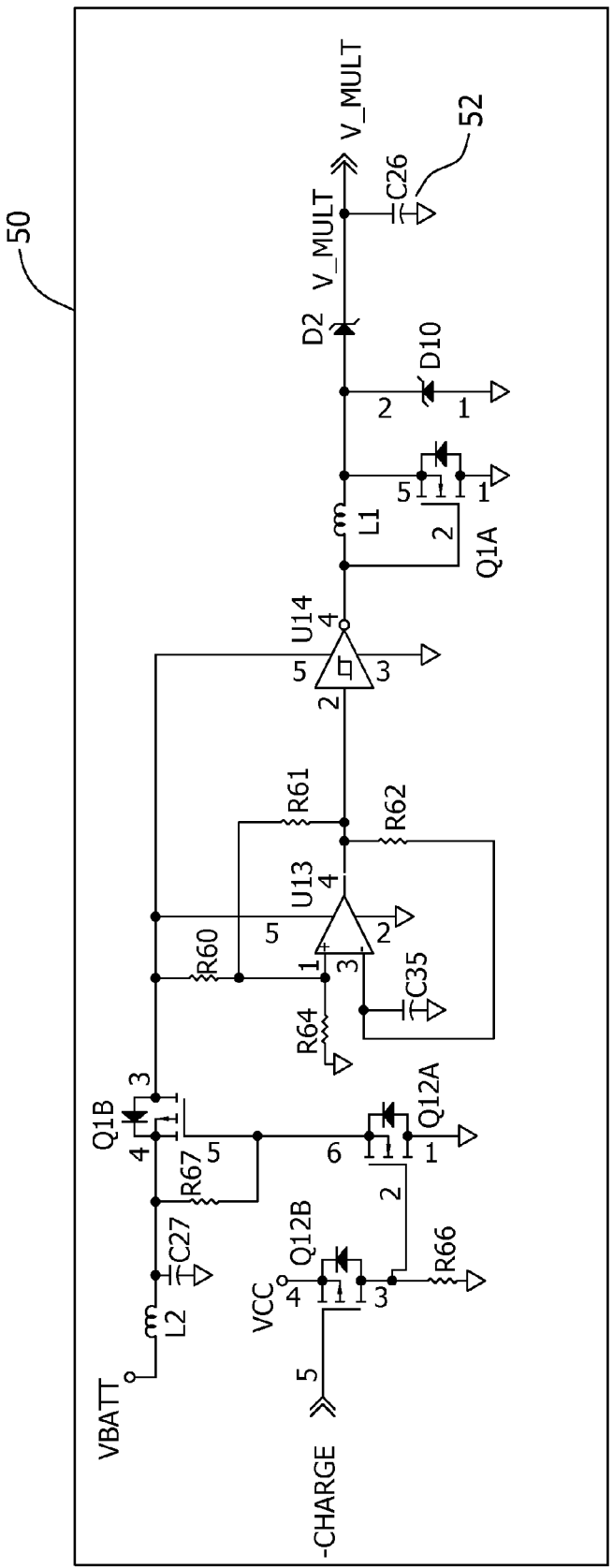
FIG. 2 is a schematic of one embodiment of a capacitor charging circuit.

FIG. 2 is a schematic of one embodiment of capacitor charging circuit 50. Referring to individual components within capacitor charging circuit 50, Q1B is a high side power switch for capacitor charging circuit 50 and the combination of Q12A and Q12B act as a level shifter. Inductor L2 acts to both limit the inrush current when Q1B is first turned ON and in conjunction with C27, helps reduce the load any switching transients place on battery 40.

U13 and the components associated with U13 form an oscillator whose frequency is determined primarily by the RC combination of C35 and R62. R60 and R64 establish the midpoint, or threshold, of the comparator and R61 provides the hysteresis that establishes upper and lower limits of a pseudo-triangular wave found at the negative input of U13. Since the output voltage, midpoint and hysteresis limits will all track changes in VBATT, the frequency is fairly constant over the life of battery 40.

L1, D2, C26, and Q1A form a voltage boost circuit. C26 is the charge capacitor (capacitor 52), which can be charged to a voltage equal to or greater than the voltage required to operate the valve driver circuits 32 and 34. D10 is a zener diode whose purpose is to protect C26 against an overcharge which would destroy the tantalum capacitor utilized as one embodiment of C26.

U14 supplies current to L1 and controls the gate of Q1A. U14 also limits the current into the voltage boost circuit. For example, when the oscillator of U13 is stopped and the output of U14 is high (logical one), if U14 were a low impedance switch, the only limit to the current in the path from VBATT-L2-Q1B-U14-L1-Q1A is the low resistances of the inductor windings and an on resistance associated the FETs (Q1A and Q1B). Because the output voltage of U14 will drop with an increased output current, the on resistance of Q1A will increase. The combination of limited output drive from U14 and the increased on resistance of Q1A combine to limit the current in the path to a much lower value than would otherwise be seen.

Figure 3:
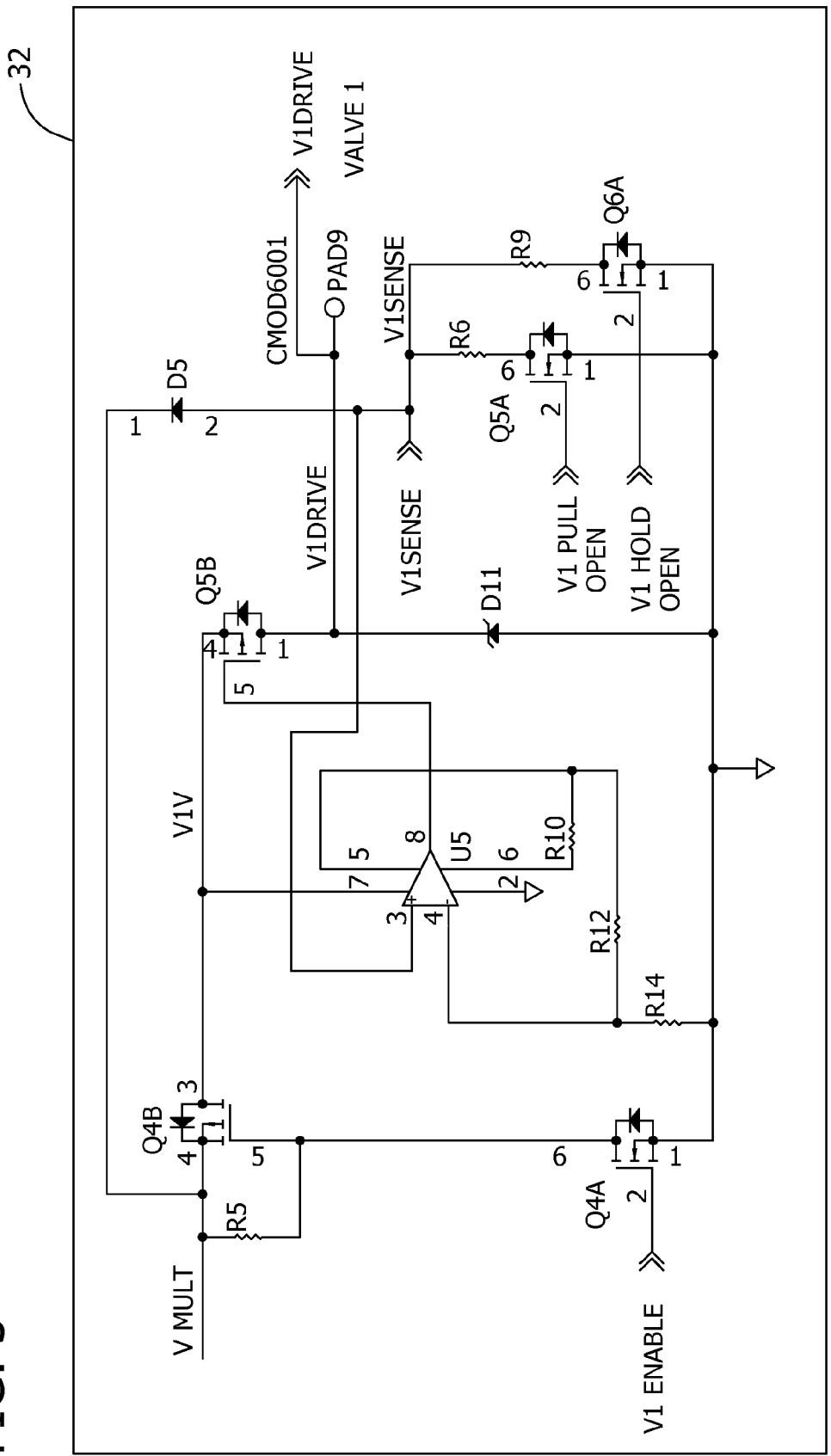
FIG. 3 is a schematic of a valve drive circuit associated with an inlet valve of an implantable pump.
Figure 4:
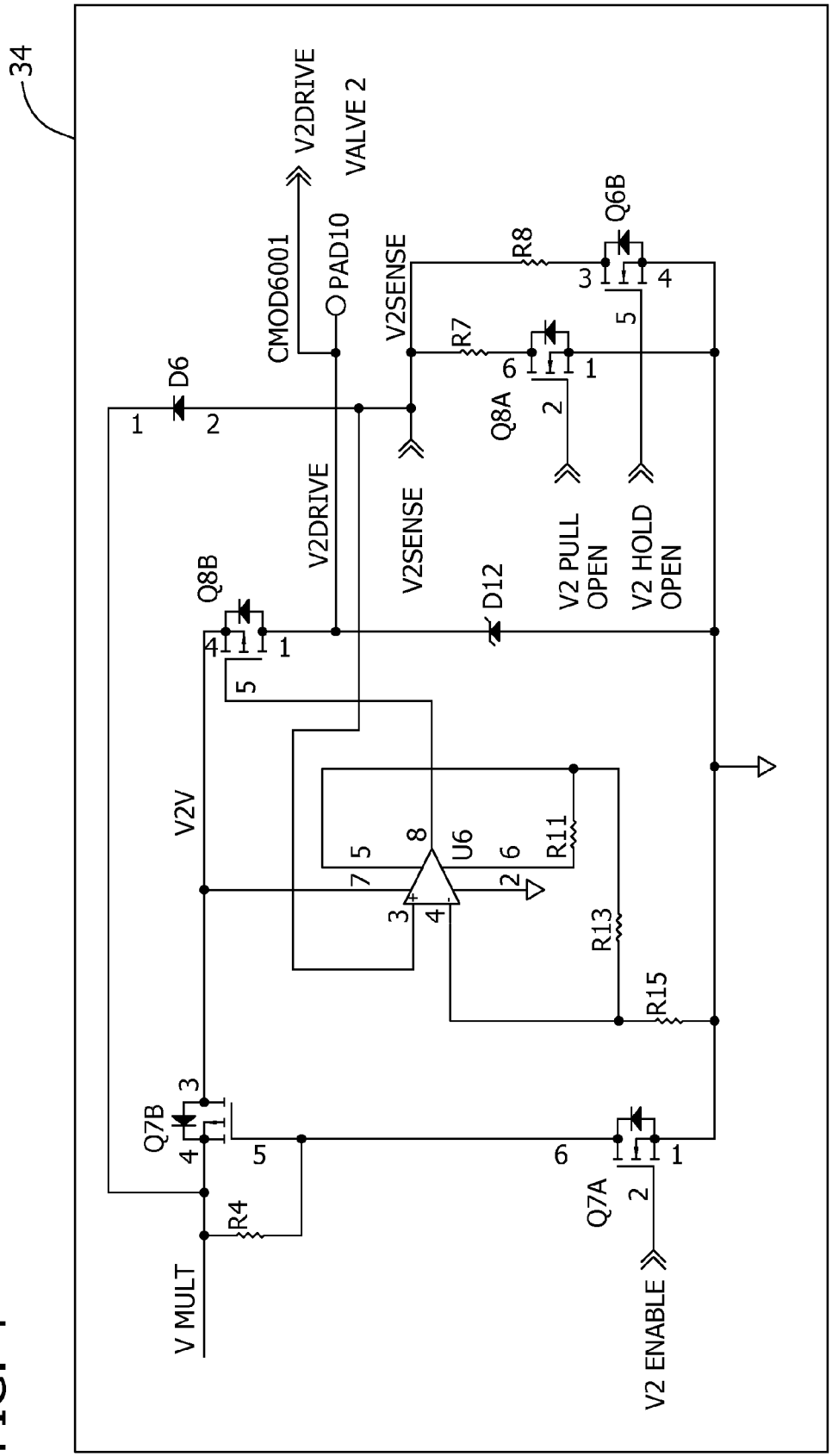
FIG. 4 is a schematic of a valve drive circuit associated with an outlet valve of the implantable pump.

FIG. 3 is a schematic of one embodiment of valve drive circuit 32, which is associated with inlet valve 22 of implantable pump 10 (both shown in FIG. 1) and FIG. 4 is a schematic of one embodiment of valve drive circuit 34, which is associated with outlet valve 24 of implantable pump 10 (both shown in FIG. 1). Valve drive circuits 32 and 34 are identical electrically, but both schematics are provided for illustration of the signals associated with the respective valves 22 (V1DRIVE in FIG. 3) and 24 (V2DRIVE in FIG. 4).

Each of valves 22 and 24 has three logic signals that control valve operation. For example, the signal Venable controls power to a driver within the valve drive circuit, the signal Vhold controls a FET switch (Q6A in FIG. 3 and Q6A in FIG. 4) that allows valve current to flow in the hold resistor (R9 in FIG. 3 and R8 in FIG. 4), and the signal Vpull allows current to flow in the pull resistor (R6 in FIG. 3 and R7 in FIG. 4).

As seen in FIGS. 3 and 4, the Vhold and Vpull paths are parallel. The hold resistor is sized so that the hold current produces a voltage at the reference point (V1SENSE in FIG. 3 and V2SENSE in FIG. 4) of the valve driver circuit. The pull resistor is used in combination with the hold resistor such that the pull open current produces the same voltage across the parallel combination as the hold open current does for the hold resistor alone.

Figure 5:
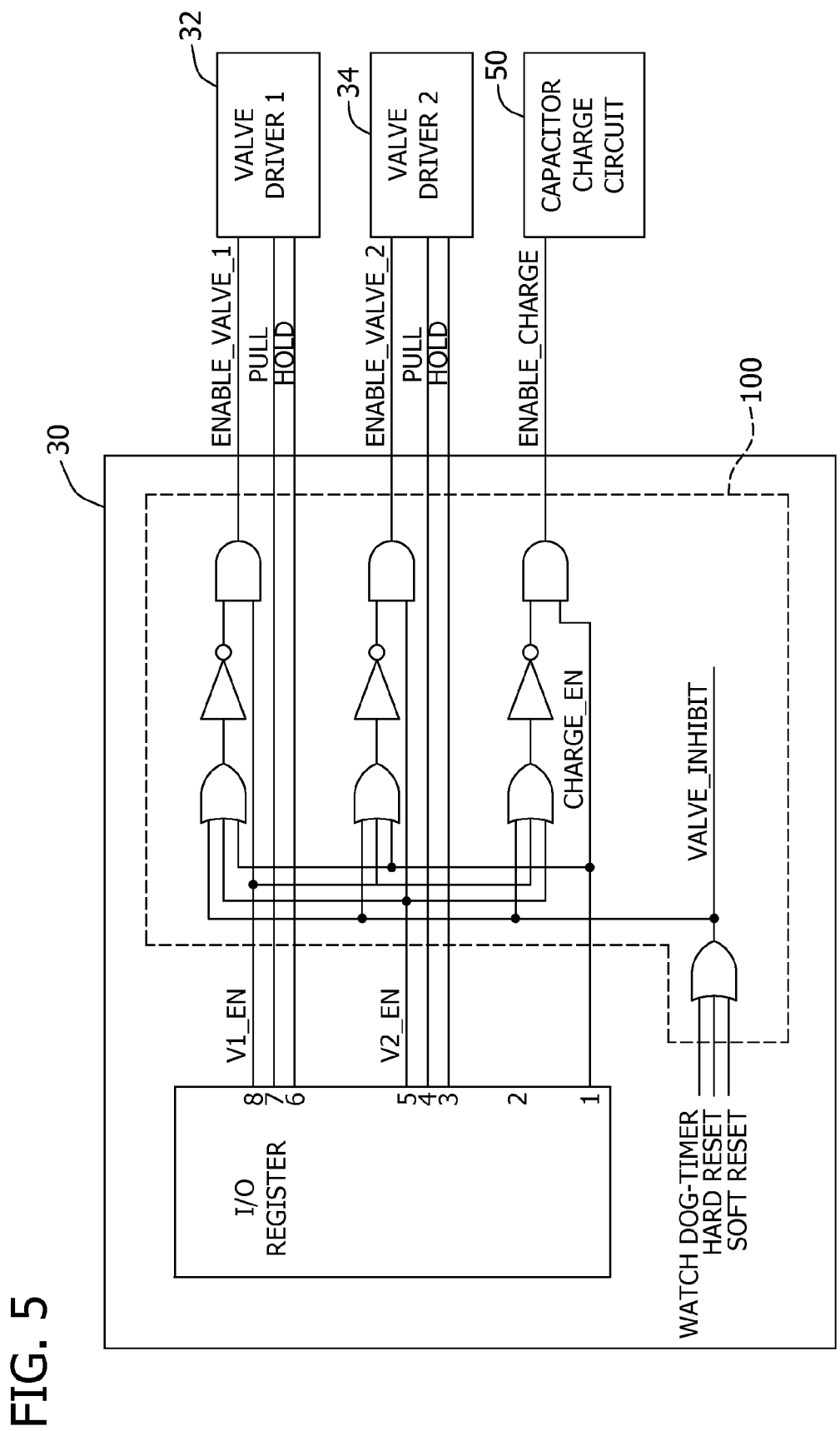
FIG. 5 is a diagram illustrating a portion of the logic between a processing device and valve driver circuits.

In an exemplary embodiment, neither valve 22, nor valve 24, is operable while charge capacitor circuit 50 (shown in FIG. 2) is in the process of charging. Such a configuration prevents battery 40 from directly supplying current to valve driver circuits 32 and 34 and therefore valves 22 and 24. To provide further assurance of desired operation, valve driver circuits 32 and 34 are not operable at the voltage supplied by battery 40. In addition, and referring to FIG. 5, valves 22 and 24 are not allowed to be simultaneously active due to the logic associated with valve driver circuits 32 and 34. Finally, capacitor charging circuit 50 cannot be active if one of valve driver circuits 32 and 34 are active. More specifically, FIG. 5 is a logic diagram that illustrates further restrictions on valve activation that are enforced by hardware. For example, a valve driver circuit 32, 34 cannot activate a valve or the charge circuit may not be active if the watchdog timer count has expired, if the hard reset flag is set, or if the soft reset flag is set.

The logic signals that control valve actuation are taken, for example, from I/O register 80 that isset up within programmable device 30. In the exemplary embodiment, logic 100 is inserted between these registers and the output pins of programmable device 30 to deactivate the valve control signals if any condition is not met. In a specific example, the V1_EN output of I/O register 80, as well as signals HARD_RESET, SOFT_RESET, WATCHDOG_BARKING, CHARGE_EN, and V2_EN are logically ANDed within logic 100, and the logical conditions enforced by this hardware must be met before valve driver circuit 32 is activated. Similar logic is utilized with the V2_EN signal for activation of valve driver circuit 34. In the illustrated embodiment, logic 100 receives the HARD_RESET, SOFT_RESET, WATCHDOG_TIMER signals generated within the programmable device 30, and generates a VALVE_INHIBIT signal which, in combination with the V1_EN and V2_EN signals, properly activates valve driver circuits 32 and 34 as described herein.

As shown in FIG. 5, pull and hold signals for each valve driver circuit are not gated in the manner described in the preceding paragraph. Such a configuration allows the path from the valve return to ground to be completed while the high side driver is disconnected, allowing any short circuit current to be detected in an inactive valve while the active valve is being driven.

With regard to programmable device 30, newer processors have been developed in response to the demand for highly capable, low-power circuits for use in handheld devices. For example, one such device includes a processor within an ASIC plus an amount of RAM, an analog-to-digital converter (ADC), and reset circuitry all within a relatively small package. One such processor is a member of the Texas Instruments MSP430 family and includes a sleep mode current of less than 100 nano-amperes (nA), a real time clock chip with an alarm that uses a 32768 Hz crystal and has a sleep mode current of less than 500 (nA). The main task of the ASIC is to keep track of time and to schedule and perform tasks at specific times. (e.g. activate valves 22 and 24 at a regular interval).

In one embodiment, an additional function performed by programmable device 30 is communication with an external programmer, for example, for changing the length of time between metered doses of a compound. In a specific embodiment, programmable device 30 includes a radio frequency communications ability, and more specifically, the ability to create a RF link in the sub-GHz bands. As such, an external transmitting device may be utilized in the reprogramming of programmable device 30, which results in, for example, one or more changes in the above described operation of pump 10. Two examples of such a change are extending the time that outlet valve 24 is open, or lessening the time between closure of inlet valve 22 and the opening of outlet valve 24. In an embodiment, communications between the external device and programmable device 30 of pump 10 are conducted using the full Medical Implant Communication standard.

Figure 6:
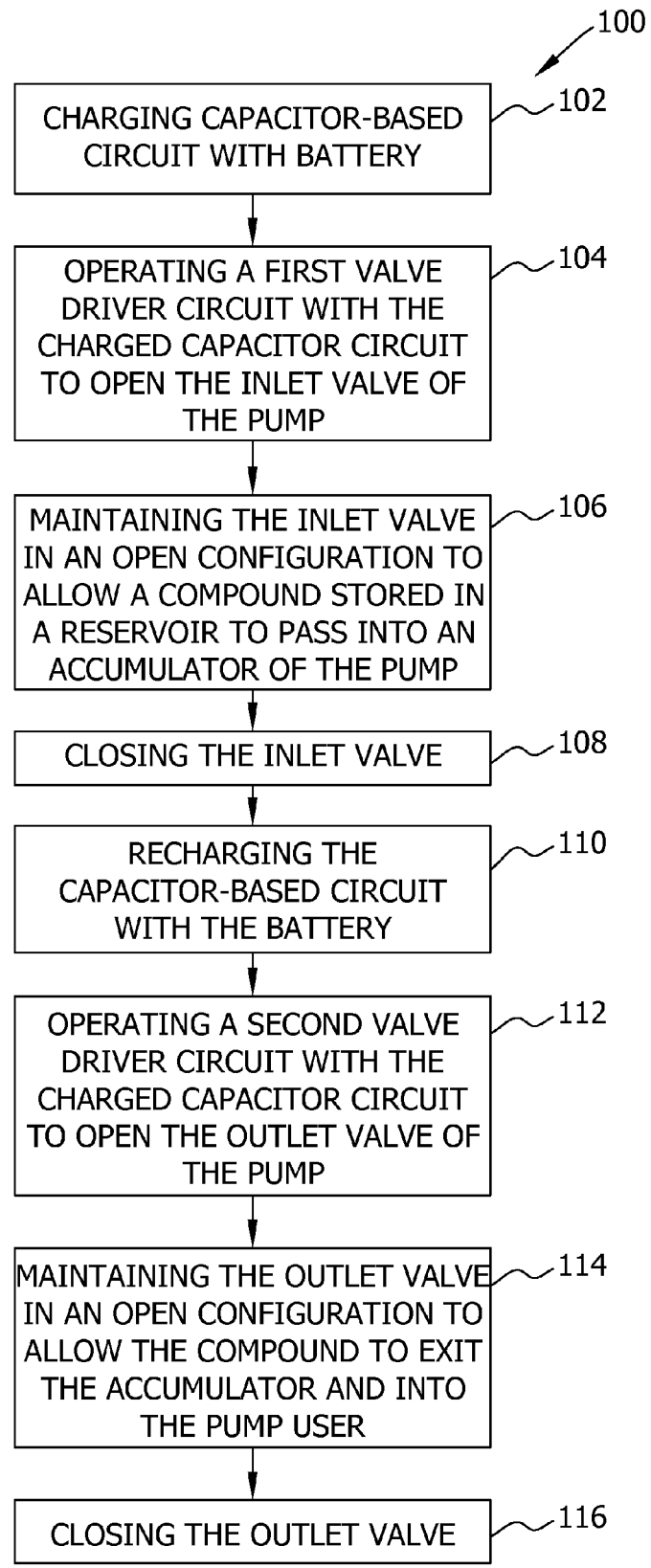
FIG. 6 is a flowchart illustrating operation of the implantable pump of FIGS. 1-5.

FIG. 6 is a flowchart 100 that illustrates a method for operating an implantable pump. As described above, implantable pump 10 includes inlet valve 22, outlet valve 24, inlet valve driver circuit 32 operating inlet valve 22 and outlet valve driver circuit 34 operating outlet valve 24, a capacitor charging circuit 50 for supplying a voltage to valve driver circuits 32 and 34, and a battery 40 which provides power to various components of pump 10 as described elsewhere herein.

Referring to flowchart 100, the method includes charging 102 capacitor charging circuit 50 with battery 40, operating 104 a first of the valve driver circuits with capacitor charging circuit 50 to open inlet valve 22, maintaining 106 the inlet valve in an open configuration to allow a compound stored in a reservoir to pass into an accumulator, and closing 108 inlet valve 22. The method continues with once again charging 110 capacitor charging circuit 50 with battery 40, operating 112 a second of the valve driver circuits with capacitor charging circuit 50 to open outlet valve 24, maintaining 114 outlet valve 24 in an open configuration to allow a compound stored in the accumulator to pass into a user of implantable pump 10, and closing 116 outlet valve 24.

The above described embodiments relate to an implantable pump for applying one or more compounds to a user who has had the pump implanted within their body for treatment of one or more conditions. The described pump, while capable of providing a constant flow through programming of the programmable device therein, is generally of the type that is described as being programmable. Generally, an indwelling catheter is connected to the pump to establish a fluid path from the pump, which is disposed subcutaneously, to a desired anatomical site. Pump operation is dictated through programming of a programmable device, as well as through the hardware limitations described above, so that individual metered doses of one or more compounds may be administered to an individual. Individual, and exclusive, operation of an inlet and an outlet valve provide assurance that the correct amount of the compound is administered to the individual at the desired times. Use of a capacitor charging circuit to operate these valves, at a voltage that is greater than a voltage supplied by the pump battery provides additional control of valve operation.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An implantable pump for providing metered doses of a compound to an individual, said implantable pump comprising:
   a chamber for storing an individual dose of the compound;
   an inlet valve fluidly coupled to said chamber for controlling a flow of the compound into said chamber, wherein said inlet valve is an electrically actuated valve;
   an inlet valve driver circuit electrically coupled to said inlet valve and operable for opening and closing said inlet valve;
   an outlet valve fluidly coupled to said chamber for controlling a flow of the compound out of said chamber and into the individual, wherein said outlet valve is an electrically actuated valve;
   an outlet valve driver circuit electrically coupled to said outlet valve and operable for opening and closing said outlet valve;
   a battery;
   a charging circuit comprising a capacitor, said charging circuit operatively coupled to said battery for charging of said capacitor, said capacitor, when charged, operable for supplying power to said inlet valve driver circuit and said outlet valve driver circuit; and
   an interlock circuit, wherein said interlock circuit is operable to prevent said inlet valve driver circuit from electrically actuating the inlet valve to open the inlet valve and to prevent said outlet valve driver circuit from electrically actuating the outlet valve to open the outlet valve during the same time interval.

2. An implantable pump according to claim 1 further comprising a programmable device programmed to:
   cause said inlet valve driver circuit to open said inlet valve;
   cause said inlet valve driver circuit to close said inlet valve after a predetermined length of time has passed since said inlet valve driver circuit caused said inlet valve to open;
   cause said outlet valve driver circuit to open said outlet valve a predetermined length of time after causing said inlet valve driver circuit to close said inlet valve; and
   cause said outlet valve driver circuit to close said outlet valve after a predetermined length of time has passed since said outlet valve driver circuit caused said outlet valve to open.

3. An implantable pump according to claim 2 wherein said programmable device comprises a wireless interface, said programmable device is reprogrammable via instructions received via said wireless interface.

4. An implantable pump according to claim 3 wherein the instructions include:
   instructions to be executed by said programmable device that set an amount of time said inlet valve driver circuit causes said inlet valve to be open;
   instructions to be executed by said programmable device that set an amount of time said outlet valve driver circuit causes said outlet valve to be open;
   instructions to be executed by said programmable device that set an amount of time between closure of said inlet valve and opening of said outlet valve; and
   instructions to be executed by said programmable device that set an amount of time between closure of said outlet valve and opening of said inlet valve.

5. An implantable pump according to claim 1 wherein the interlock circuit is operable to prevent said inlet valve driver circuit and said outlet valve driver circuit from being actuated during a time interval when said battery is charging said capacitor.

6. An implantable pump according to claim 1 wherein said charging circuit is operable to charge said capacitor to a voltage that is greater than a voltage associated with said battery.

7. An implantable pump according to claim 6 wherein the voltage level to which said capacitor is charged is a voltage level compatible with operation of said inlet valve driver circuit and said outlet valve driver circuit.

8. An implantable pump according to claim 1 wherein said charging circuit is operable to prevent said battery from directly supplying current to said inlet valve driver circuit and said outlet valve driver circuit.

9. A method for operating an implantable pump, the implantable pump including an inlet valve, an outlet valve, an inlet valve driver circuit, an outlet valve driver circuit, a charging circuit that includes a storage capacitor for supplying a voltage to the valve driver circuits, an interlock circuit, and a battery for operating the charging circuit, said method comprising:
   charging the capacitor in the charging circuit using the battery;
   operating the inlet valve driver circuit, using the charged capacitor, to electrically open the inlet valve, wherein said inlet valve is an electrically actuated valve;
   maintaining the inlet valve in an open configuration to allow a compound stored in a reservoir to pass into an accumulator;
   operating the inlet valve driver circuit to electrically close the inlet valve;
   charging the capacitor in the charging circuit using the battery;
   operating the outlet valve driver circuit, using the charged capacitor, to electrically open the outlet valve, wherein said outlet valve is an electrically actuated valve;
   maintaining the outlet valve in an open configuration to allow a compound stored in the accumulator to pass into a user of the implantable pump;
   operating the outlet valve driver circuit to electrically close the outlet valve; and
   preventing the inlet valve driver circuit from using the charged capacitor to electrically open the inlet valve and preventing the outlet valve driver circuit from using the charged capacitor to electrically open the outlet valve during the same time interval using the interlock circuit.

10. A method according to claim 9 wherein:
    operating the inlet valve driver circuit to close the inlet valve comprises causing the inlet valve driver circuit to close the inlet valve after a predetermined length of time has passed since the inlet valve driver circuit caused the inlet valve to open; and operating the outlet valve driver circuit to close the outlet valve comprises causing the outlet valve driver circuit to close the outlet valve after a predetermined length of time has passed since the outlet valve driver circuit caused the outlet valve to open.

11. A method according to claim 9 further comprising preventing at least one of the inlet valve driver circuit and the outlet valve driver circuit from being actuated during a time interval when the battery is charging the capacitor through the charging circuit.

12. A method according to claim 9 wherein charging the capacitor in the charging circuit using the battery comprises increasing a voltage associated with the battery for storage within the capacitor.

13. A method according to claim 9 wherein charging the capacitor in the charging circuit using the battery comprises preventing the battery from directly supplying current to the valve driver circuits.

14. A circuit for controlling operation of an electrically actuated inlet valve and an electrically actuated outlet valve of an implantable pump, the electrically actuated inlet valve operable to allow a metered dose of a compound to pass from a reservoir to an accumulator, the electrically actuated outlet valve operable to allow the metered dose to pass from the accumulator into a user of the implantable pump, said circuit comprising:
   an inlet valve driver circuit operable for opening and closing the electrically actuated inlet valve;
   an outlet valve driver circuit operable for opening and closing the electrically actuated outlet valve;
   a battery;
   a charging circuit comprising a capacitor, said charging circuit operatively coupled to said battery for charging of said capacitor, said capacitor operable for supplying power to said inlet valve driver circuit and said outlet valve driver circuit and further operable for preventing said battery from directly supplying current to said inlet valve driver circuit and said outlet valve driver circuit; and
   an interlock circuit operable to prevent said inlet valve driver circuit from electrically actuating the inlet valve to open the inlet valve and to prevent the outlet valve driver circuit from electrically actuating the outlet valve to open the outlet valve during the same time interval.

15. A circuit according to claim 14 wherein said charging circuit is operable to increase a voltage associated with said battery for storage within said capacitor.

16. A circuit according to claim 14 further comprising a programmable device operable to:
   execute instructions that control an amount of time said inlet valve driver circuit causes the electrically actuated inlet valve to be open;
   execute instructions that control an amount of time said outlet valve driver circuit causes the electrically actuated outlet valve to be open;
   execute instructions that control an amount of time between operating said inlet valve driver circuit to close the electrically actuated inlet valve and operating said outlet valve driver circuit to open the electrically actuated outlet valve; and
   execute instructions that control an amount of time between operating said outlet valve driver circuit to close the electrically actuated outlet valve and operating said inlet valve driver circuit to open the electrically actuated inlet valve.

17. A circuit according to claim 14 further comprising a programmable device operable to control operation of said inlet valve driver circuit, said outlet valve driver circuit, and said charging circuit, said programmable device comprising a wireless interface, said programmable device reprogrammable based on instructions received at said wireless interface.

* * * * *